United States Patent [19]

Metcalfe et al.

[11] Patent Number: 4,596,738
[45] Date of Patent: Jun. 24, 1986

[54] POLYMER BLEND FILMS

[75] Inventors: Peter J. Metcalfe, Cottingham; Andrew J. Carter, Sawbridgeworth, both of United Kingdom

[73] Assignee: Smith and Nephew Associated Companies p.l.c., United Kingdom

[21] Appl. No.: 661,734

[22] Filed: Oct. 17, 1984

[30] Foreign Application Priority Data

Oct. 22, 1983 [GB] United Kingdom ............... 8328279

[51] Int. Cl.$^4$ .................. B32B 5/18; A61L 15/00
[52] U.S. Cl. ..................... 428/308.4; 428/315.5; 428/319.3; 428/131; 128/156; 604/370
[58] Field of Search ............. 428/131, 158, 308.4, 428/315.5, 319.3; 128/156; 604/370, 897

[56] References Cited

U.S. PATENT DOCUMENTS

| Re. 31,886 | 5/1985 | Hodgson | 428/40 |
| Re. 31,887 | 5/1985 | Hodgson | 428/355 |
| 3,387,077 | 6/1968 | Sammons et al. | 428/131 |
| 3,645,835 | 2/1972 | Hodgson | 428/195 |
| 3,939,237 | 2/1976 | Naito et al. | 521/81 |
| 4,105,737 | 8/1978 | Suzuki | 264/154 |
| 4,381,326 | 4/1983 | Kelly | 604/336 |
| 4,452,845 | 6/1984 | Lloyd et al. | 128/156 |
| 4,483,965 | 11/1984 | Ohba et al. | 525/322 |

FOREIGN PATENT DOCUMENTS

| 914489 | 1/1963 | United Kingdom . |
| 1055963 | 1/1967 | United Kingdom . |
| 1075487 | 7/1967 | United Kingdom . |
| 1110051 | 4/1968 | United Kingdom . |
| 2081721 | 2/1982 | United Kingdom . |
| 2103537 | 2/1983 | United Kingdom . |

Primary Examiner—John E. Kittle
Assistant Examiner—Thomas C. Saitta
Attorney, Agent, or Firm—Jacobs & Jacobs

[57] ABSTRACT

A moisture vapor transmitting elastomeric film which comprises a blend of incompatible polymers and contains voids characterized in that the blend comprises a continuous matrix of ethylene vinyl acetate within which the incompatible polymer forms a discrete particulate phase matrix, processes for the preparation thereof and articles comprising these films are described.

15 Claims, No Drawings

POLYMER BLEND FILMS

The present invention relates to moisture vapour transmitting elastomeric films, processes for their preparation and articles comprising these films.

Elastomeric films possess good conformability and are therefore suitable for use in bodily contact articles such as dressings for example wound dressings, to provide such articles with good conformability to the skin. Desirably the elastomeric film should be moisture vapour transmitting to prevent for example maceration of the skin under the dressing.

Moisture vapour transmitting elastomeric films which contain voids and comprise a blend of polyurethane and an incompatible polymer are disclosed in British Patent Application No. 2,081,721A and European Patent Application No. 096458. Polyurethane films however, are relatively expensive to manufacture. It would therefore be desirable to have suitable elastomeric films of a polymer which is less expensive than polyurethane. Unfortunately, films of such elastomers tend to have poor moisture vapour transmission properties. British Patent Application No. 2,103,537A discloses a moisture vapour transmitting elastomeric film, suitable for use in adhesive medical dressings, which contain voids and comprises a blend of 1,2 polybutadiene and an incompatible polymer. Such a film although more economical to manufacture than a polyurethane film has relatively poor moisture transmission properties without the provision of apertures in the film. Ethylene vinyl acetate copolymers are known to have elastomeric properties. Conventional ethylene vinyl acetate copolymer films, however, have moisture vapour transmission rates which are less than desirable for dressings. U.S. Pat. No. 4,381,326 discloses an elastic reticulated sheet which comprises a blend of ethylene vinyl acetate copolymer and a block copolymer of styrene and butadiene or isoprene. The blends disclosed in this patent, however, do not contain more than 10% by weight of ethylene vinyl acetate copolymer.

Elastomeric films of ethylene vinyl acetate copolymer have now been found which have improved moisture vapour transmission rates and which are suitable for use in bodily contact articles such as wound dressings.

Accordingly the present invention provides a moisture vapour transmitting elastomeric film which comprises a blend of incompatible polymers and contains voids characterised in that the blend comprises a continuous matrix of ethylene vinyl acetate within which the incompatible polymer forms a discrete particulate phase.

The films of the invention are especially suitable for wound dressings.

The term "voids" when used herein means small holes within the film. These small holes may interrupt the surface of the film or coalesce but do not provide a continuous pathway through the film.

Continuous films of the invention therefore will be impermeable to liquid water.

Accordingly in a favoured aspect the film of the invention is a liquid water impermeable film.

The liquid water impermeable film of the invention can be used advantageously in wound dressings, for example as a backing layer in adhesive dressings. Such a film can provide a dressing when used over a wound with a barrier to bacteria and liquid water penetrating from the outside of the dressing to the wound surface. Liquid water impermeable films of the invention for use in wound dressings suitably have a moisture vapour transmision rate of at least 200 g/m$^2$, more suitably a rate of at least 350 g/m$^2$, desirably a rate of at least 500 g/m$^2$ and preferably at least 1000 g/m$^2$/24hrs at 37° C. at 100% to 10% relative humidity difference.

The liquid water impermeable films of the invention suitably have a thickness of 0.05 to 0.25 mm, desirably 0.05 to 0.20 mm and preferably have a thickness of 0.075 to 0.125 mm.

The voided films of the invention can have apertures. Thus in a further preferred aspect the film of the invention is an apertured film.

The apertured films of the invention will allow the passage of water in liquid or vapour form and therefore can be used in wound dressings to provide a high moisture vapour transmission rate and to allow the passage of wound exudate and in sanitary absorbent pads to allow the transmission of body exudate fluids.

In a favoured aspect the elastomeric apertured film of this invention is in the form of a net. When used herein the term "net" means a structure having a set of ribs. Suitably the ribs of the net are parallel. Also suitably the ribs of the net may be serpentine and touch or join each other intermittently. More suitably the nets of this invention will have at least two sets of parallel ribs which sets intersect or are skew to each other. Most suitably the nets of this invention will have two sets of parallel ribs which sets are perpendicular to each other.

The nets of this invention will frequently contain membranes extending outwardly from the ribs to define the aperture. Whether the aperture is defined by such membranes or by the ribs per se, it is believed that the area of aperture to the total area of the film is suitably 5 to 75%, more suitably 10 to 50% and is preferably 20 to 40%.

Nets of this invention will suitably contain at least one set of ribs which are from 0.03 to 2.5 mm thick, more suitably 0.05 to 1 mm and preferably from 0.05 to 0.5 mm thick in the direction of thickness of the film.

The nets of this invention maybe used as backings for dressings, as wound facing layers and as cover layers on sanitary absorbent pads such as sanitary towels, diapers; incontinence pads and the like.

The holes or apertures in the apertured films of the invention may suitably have an approximately elliptical shape (for a uniaxially stretched film) or an approximately circular shape (for a biaxially stretched film).

It is desirable that the films of this invention have a recoverable elastic strain of at least 25%, more suitably at least 50% and preferably at least 100%.

The films of the invention are normally opaque due to the voids in the body of the film.

The films of the invention have a desirable soft surface feel when they are used in the manufacture of articles for bodily contact.

Suitable ethylene vinyl acetate copolymers for use in the films of the invention comprise 3% to 40% by weight and preferably 5% to 30% by weight of vinyl acetate residues. Favoured ethylene vinyl acetate copolymers of this type are known as EVATANE (trade mark) Nos. 555, 539, 24-03 and 28-05 available from Imperial Chemical Industries Limited. EVATANE 555, 539, 24-03 and 28-05 contain respectively 12.5%, 18%, 24% and 28% by weight of vinyl acetate residues.

The ethylene vinyl acetate copolymer can contain additives such as fillers and antioxidants.

The incompatible polymer used in the film of the invention forms a discrete particulate phase within a continuous matrix of the ethylene vinyl acetate copolymer.

It is preferred that the particles of the discrete particulate phase of incompatible polymer should be spherical or ellipsoidal in shape and have a diameter of at least 0.25 micro meters, for example 0.5 micro meters to 5 micro meters.

It is desirable that mechanical and physical properties of the incompatible polymer are significantly different from that of the ethylene vinyl acetate copolymer at temperatures at which the film will cold draw. It is particularly desirable that the incompatible polymer should have a higher modulus than that of the ethylene vinyl acetate copolymer at cold draw temperatures.

Suitable incompatible polymers include those derived from the polymerisation of vinyl aromatic hydrocarbons. An especially suitable incompatible polymer is polystyrene. The polystyrene may be an unmodified (homopolymer) or rubber modified grade that is a high impact polystyrene. High impact polystyrene is a preferred incompatible polymer.

A preferred high impact polystyrene is known as Styron 485 supplied by Dow Chemicals.

The proportions of ethylene vinyl acetate copolymer and the incompatible polymer in the blend depend to some extent on the individual polymers. However in general suitable blends contain 40% to 95% by weight, desirably 45% to 90% by weight and preferably 50% to 85% by weight of ethylene vinyl acetate copolymer.

A preferred blend for water impermeable films of the invention contains 60% by weight of ethylene vinyl acetate copolymer (for example Evatane 555 or 28-05) and 40% by weight of incompatible polymer (for example high impact grade polystyrene such as Styron 485).

A preferred blend for apertured films of the invention contains 80% by weight of ethylene vinyl acetate copolymer (for example Evatane 539 or 24-03) and 20% by weight of incompatible polymer (for example high impact polystyrene such as Styron 485).

The films of this invention are suitable for use in articles for bodily contact. Thus in a further aspect the invention provides an article for bodily contact which comprises a film of the invention.

Bodily contact articles of the invention include dressings such as wound dressings and hygienic absorbent pads, such as sanitary towels, diapers, incontinence pads and alike pads. It is preferred however that the bodily contact article is a wound dressing.

Most aptly the films of this invention are used as the backing in an adhesive wound dressing such as a first aid dressing. Such wound dressings form part of this invention.

It is preferred that adhesive dressing of the invention have a moisture vapour transmission rate of at least 150 $g/m^2$, suitably at least 250 $g/m^2$ and preferably at least 500 $g/m^2/24hrs$ at 37° C. at 100% to 10% relative humidity difference.

The moisture vapour transmission rate may be measured by the Payne Cup method. The method uses a cup 1.5 cm deep with a flanged top. The inner diameter of the flange is such to provide an area for moisture vapour transmission of 10 $cm^2$. In this method 10 ml of distilled water is added to the cup and a sample of the material under test, large enough to completely cover the flange, is clamped over the cup. The complete assembly is then weighed and placed in a cabinet where the temperature and relative humidity are maintained at 37° C. and 10% respectively. After 17 hours the cup is removed from the cabinet and allowed to cool at room temperature. After re-weighing, the mass of water lost by vapour transmission is calculated and the result expressed as in $g/m^2/24hrs$ at 37° C. at 100% to 10% relative humidity difference.

The adhesive layer can be discontinuous for example in the form of porous (including microporous) or patterned coated layers. However it is preferred that the adhesive layer is continuous.

Suitable continuous adhesive layers can comprise an acrylate ester copolymer or a polyvinyl ether. Preferred acrylate ester copolymer adhesives are disclosed in United Kingdom Application No. 2070631. A favoured acrylate ester copolymer adhesive is a copolymer of 47 parts by weight of 2-ethylhexyl acrylate, 47 parts by weight of n-butyl acrylate and 6 parts by weight of acrylic acid with a K value of 95 polymerised in acetone according to the method given in the above application.

Suitably the thickness of the adhesive layer of adhesive dressing of the invention can be from 12.5 micro meters to 75 micro meters. Suitable thicknesses of the film backings of adhesive dressings of the invention are described hereinbefore in relation to films of the invention.

A wound dressing of this invention can have an absorbent pad covered with a non-adherent wound facing layer as is conventional in dressings of this type.

In a further aspect the invention provides a process for making a film of this invention which comprises forming a film from a blend of ethylene vinyl acetate copolymer and an incompatible polymer, cold drawing (that is stretching at 10° to 60° C.) the film until voiding occurs and allowing the drawn film to contract.

The apertured films, including the nets of this invention maybe prepared by forming an ethylene vinyl acetate copolymer/ incompatible polymer blend film having thicker and thinner areas and stretching that film until apertures are formed. During stretching voiding of the film occurs which is then followed by rupture of the thinner areas to form apertures.

The thicker and thinner areas in the film can be conveniently formed by embossing.

Generally overall thickness of the embossed film will be from 0.09 to 7.5 mm thick, more suitably from 0.15 to 3.5 mm thick and preferably from 0.15 to 1.5 mm thick. More suitably the thinner parts of the film employed will be from 0.02 mm to 0.5 mm thick, more suitably from 0.010 mm to 0.01 mm thick and preferably from 0.005 mm to 0.075 mm thick.

The pattern of thicker and thinner areas provided on the film to be stretched will be chosen to ensure that undue propagation of the rupture will be prevented. Suitable patterns thus include those set forth in British Patent Nos. 914489, 1055963, 1075487 and 1110051.

It is preferred that the film is formed by a hot melt process in particular by hot melt extrusion. It is also preferred that the blending of ethylene vinyl acetate copolymer and the incompatible polymer is carried out under hot melt conditions, for example, using a heated blade mixer or a compounding extruder although premixing of the granules can be carried out by tumbling at room temperature.

The materials used in the process of the invention can be the materials described hereinbefore in relation to the film of the invention.

The liquid impermeable and apertured films of the invention can be prepared by the general processes given in the aforementioned British Patent Application No. 2,081,721A and European Patent Application No. 096458 which are incorporated herein.

In a process for preparing a water impermeable film of the invention it is preferred that casting rollers have a plain surface.

In a process for preparing an apertured film of the invention one or both of the casting rollers can have a surface pattern of raised or depressed areas to provide a corresponding pattern of thicker and thinner areas on one or both sides of the blend film.

The extruded ethylene vinyl acetate copolymer and incompatible blend film is stretched to form the elastomeric film containing voids. The stretching should be carried out at cold draw temperatures for example 10° C. to 60° C., preferably at 15° C. to 30° C. The stretching can take place longitudinally or transversely to the extrusion direction or in both such directions either simultaneously or sequentially. It is preferred that the film is stretched in both the longitudinal and transverse direction to provide the film with a better balance of physical properties and also to increase the area of the apertures in the apertured film. It is preferred that the film should be given a stretch of between 100% to 500%. The degree of stretching should be greater than the yield elongation but less than the elongation at break of the film at cold draw temperatures.

After stretching the film is also allowed to contract. These stretching and relaxation stages convert the ethylene vinyl acetate copolymer-incompatible polymer blend films into an elastomeric film containing voids. These voids are normally very small with diameters of between 2 and 12 micro meters and more usually between 3 and 6 micro meters.

Films of the invention can be provided with an adhesive layer by conventional coating methods which include coating from a solution, an emulsion, by hot melt or by extrusion. The films may be coated directly or indirectly, for example by transfer from a release surface.

The wound dressings of this invention may be prepared from a film of this invention in conventional manner, for example, on conventional dressing machines.

The apertured films of this invention may be made by using methods known in the art to be suitable when employing non-elastomeric materials such as polyolefines, for example polyethylene. It is therefore surprising that the polymer blends disclosed herein can be processed by such methods since it has herebefore been generally believed that elastomeric materials could not be processed in such manner.

The invention is illustrated by the following Examples:

EXAMPLE 1

This Example describes the preparation of a liquid water impermeable film of the invention.

Preparation of Polymer Blend 60 parts by weight of an ethylene vinyl acetate copolymer (Evatane 555) and 40 parts by weight of a high impact polystyrene (Styron 485) were weighed into a blade mixer chamber (Shearmix size 4 available from Baker Perkins Limited) heated to 165° C. and mixed for 4 minutes. The resultant mix was removed from the mixer and formed into sheet (approximately 1.5 mm thick) on a heated two roll mill. The sheet was cut into strips of approximately 50 mm × 25 mm, allowed to cool and then granulated in a Masson cutter.

Extrusion of Film

A film was made by feeding the polymer blend mixture into a Brabender Extrusiograph extruder (length to diameter screw ratio of 25:1) driven by a Brabender PLE 651 plasticorder and extruding the mixture through a 150 mm film die into the nip of a two roller casting unit placed near the die. The extrusion conditions were as follows:

Die temperature: 190° C.
Screw speed: 80 revs per minute
Casting roller speed: 2.2 meters/minute
Back pressure: 1 Kilo Newton
Die gap: 0.254 mm Stretching of Film A voided film was made by stretching the cast film in a direction transverse to the machine direction on a laboratory Hounsfield tensometer. The film was stretched to a draw ratio of 4:1 (300% extension) at ambient room temperature 18° C. to 22° C. and the drawn film allowed to contract to 2.5:1 (150%) to form a film of the invention.

The voided film had a thickness of 0.114 mm and a moisture vapour transmission rate of 1450 g/m$^2$/24hrs at 37° C. at 100% to 10% relative humidity difference (Payne Cup). The film had a recoverable elastic strain of 100%. The film was found to be impermeable to liquid water.

EXAMPLE 2

This example describes the preparation of an apertured film (net) of the invention Preparation of Polymer Blend Granules of ethylene vinyl acetate copolymer (Evatane 24-03, 80 parts by weight) and high impact polystyrene (Styron 485, 20 parts by weight) were mixed by tumble blending. The mixed granules were then fed into a Brabender Extrusiograph 19 mm extruder fitted with a 25:1 length to diameter screw of a polyolefine type having a compresion ratio of 3:1 and extruded through a tubular die. The extrusion was carried out using a die temperatue of 185° C. and a screw speed of 120 rpm. The extruded tube was drawn through a water bath maintained at 20° C. at a speed to reduce the tube diameter to approximately 3 mm. After travelling a distance of approximately 1 meter through the bath, the tube was passed over a foam pad to remove excess moisture before being cut into 3 to 5 mm lengths using a laboratory model granluator (Accrapack). The granules were collected from the granulator and dried for two hours at 70° C. in an air circulating oven in trays 2.5 cm deep.

Extrusion of Film

The polymer blend granules were fed into the hopper of a Brabender Extrusiograph instrumented extruder, which was driven by a Brabender Plasticorder PLE 651 drive unit and which was equipped with a 150 mm wide flat sheet die and a polyolefine-type screw with a length to diameter ratio of 3:1. The die was maintained at a temperature of 185° C. and, using a screw speed of 55 rpm, which gave registered torque and axial back pressure measurements of 14 Nm and 1.5 KN respectively, the melt film was extruded longitudinally and fed into the nip of a two roller chill casting unit located 5 cm from the die face.

One roller of this chill casting unit was provided with one conical projection per 0.725 mm in both circumferential and axial directions. The height of these projections above the roller surface was 0.21 mm and their diameter at the roller surface was 0.42 mm. The other roller in the chill casting unit was a flat surfaced roller. The casting nip speed was 2.1 meters/minute. The film produced was 100 mm wide, had a thickness of 0.102 mm, had a weight per unit area of 72 gsm and had a pattern of conical depressions (0.36 mm diameter) on one surface which corresponded with the pattern of conical projections on the cast roller surface. The film however was not perforated.

Stretching of Film

The extruded film was stretched in a Laboratory Hounsfield tensometer. A sample of width 140 mm and length 60 mm was stretched at a ratio 2.5:1 in a direction transverse (perpendicular) to the extrusion direction (machine direction). The film was allowed to contract and a sample of width 75 mm and length 80 mm was stretched at a ratio of 2.2:1 in a direction parallel to the extrusion direction (machine direction) and allowed to contract to a ratio of 1.4:1.

The resulting film had elliptical apertures with their major axis in the machine direction. The apertures in the film varied in size from 0.42 to 0.68 mm in the major axis and from 0.28 to 0.39 mm in the minor axis. The film had a weight per unit area of 41 g/m$^2$ and a thickness of 0.066 mm.

EXAMPLE 3

The example describes the preparation of another apertured film (net) of the invention.

Preparation of Polymer Blend

The polymer blend was prepared in the same manner as Example 2 using Evatane 539 instead of Evatane 24-03.

Extrusion of film

The polymer blend film was prepared in the same manner as Example 2 using the following extrusion conditions:

Screw speed: 70 rpm
Torque: 14 Nm
Back Pressure: 1.5 KN
Casting Roller Speed: 3 meters/minute The film produced had a width of 104 mm, a thickness of 0.155 mm and a weight per unit area of 68.7 g/m$^2$. The film had a pattern of conical depressions on one surface which corresponded with the conical projections on the cast roller surface.

Stretching of the Film

The film was stretched in a similar manner to the film of Example 2 except that the transverse direction was ommitted and the film was stretched at a ratio of 2:1 in the machine direction only.

The resulting film had elliptical apertures with major axis in the machine direction. The apertures in the film had a size of approximately 0.38 mm in the major axis and approximately 0.19 in the minor axis direction. The area of the apertures was approximately 20% of the total area of the film.

EXAMPLES 4, 5 and 6

The liquid impermeable film of Example 1 and the apertured (net) films of Examples 2 and 3 were coated by means of transfer coating process with a polyacrylate adhesive (30 micro meters thick). The polyacrylate adhesive used was a copolymer of 47 parts by weight of 2-ethylhexyl acrylate, 47 parts by weight of n-butyl acrylate and 6 parts by weight of acrylic acid with a K value of 95 polymerised in acetone according to the method given in United Kingdom Application No. 2070631.

The adhesive coated films were made into adhesive first aid dressings.

EXAMPLE 7

This example describes the preparation of another liquid water impermeable film of the invention.

Preparation of Polymer blend

A polymer blend of 60 parts by weight of Evatane 28-05 and 40 parts by weight of Styron 485 was prepared in the same manner as Example 2 except that the extrusion was carried out using a die temperature of 200° C.

Extrusion of Film

A film was prepared in the same manner as Example 1 using the following extrusion conditions.

Die temperature: 200° C.
Screw speed: 31 revs per minute
Back pressure: 1.5 KN
Casting roller speed: 0.75 m/min
Casting roller temperature: 30° C.
Die gap: 0.254 mn Stretching of Film A voided film was prepared by stretching the cast film in the extrusion machine direction on a laboratory Hounsfield tensometer. The film was stretched to a draw ratio of 4.5:1 and allowed to contract to 3:1 to form a film of the invention. The voided film had a thickness of 0.125 mm and a moisture vapour transmission rate of 998 g/m$^2$/24 hr at 37° C. at 100% to 10% relative humidity difference. The film was found to be impermeable to liquid water.

EXAMPLE 8

This example describes the preparations of a further apertured film (net) of the invention.

Preparation of polymer blend

A polymer blend of 80 parts by weight of Evatane 28-05 and 20 parts by weight of Styron 485 was prepared in the same manner as example 2 using an extrusion die temperature of 2000° C. and screw speed of 118 rpm.

Extrusion of Film

The polymer blend granules were fed into the hopper of a Brabender Extrusiograph instrumented extruder, which was driven by a Brabender Plasticorder PLE 651 drive unit and which was equipped with a 150 mm wide film flex lip die and a polyolefine-type screw with a length to diameter ratio of 3:1. The die was maintained at a temperature of 200° C. and using a screw speed of 115 rpm, which gave a registered torque and axial back pressure measurements of 14 Nm and 1.5 KN respectively, the melt film was extruded vertically downwards and fed into the nip of a two roller chill casting unit located 4 cm from the die face. The casting rollers were maintained at a temperature of 40° C. and had a casting speed of 0.75 m/min.

One roller of this chill casting unit had a surface pattern of parallel ribs and grooves (1 per mm) arranged in the axial direction of the roller. The parallel ribs and grooves had a truncated triangular shape and a height or depth of 0.6 mm. The other roller had a surface pattern of parallel ribs and grooves (1 per mm) arranged in the circumferential direction of the roller. The parallel ribs and grooves of this roller had a truncated triangular shape and height or depth of 0.65 mm.

The extruded cast film had a weight per unit area of 441 g/m² and a thickness of 0.75 mm. The film had an embossed pattern of ribs and grooves (1 per mm) on one surface which intersected at right angles with a similar pattern of ribs and grooves on the other surface of the film. The areas of intersection between the embossed grooves on either side of the film provide the thin areas in the film.

Stretching of Film

The extruded film was stretched in laboratory Hounsfield tensometer. A sample film of width 120 mm and length 100 mm was stretched a draw ratio of 3:1 in the machine direction (extrusion direction). The film was allowed to contract and a sample of width 120 mm and length 80 mm was stretched at a draw ratio of 3:1 in the transverse direction (perpendicular to machine direction) to form a net of the invention.

The net had elliptical apertures with their major axis in the transverse direction. The aperture size was 1.04 mm in major axis and 0.75 mm in the minor axis. The area of the apertures in the net were 30% of the total area of the net.

The net had a weight per unit area of 63 g/m². The net exhibited two sets of intersecting parallel ribs which were perpendicular to each other.

We claim:

1. A moisture vapor transmitting elastomeric film which comprises a blend of incompatible polymers and contains voids within the film, said voids not providing a continuous pathway through the film, and wherein the blend comprises a continuous matrix ethylene-vinyl acetate copolymer within which the incompatible polymer forms a discrete particulate phase.

2. A film according to claim 1 in the form of a wound dressing.

3. A film according to claim 1 which is liquid water impermeable and has a moisture vapor transmission rate of at least 500 g/m²/24 hours at 37° C. at 100% to 20% relative humidity difference.

4. A film according to claim 1 in which the polymer blend contains 40% to 90% by weight of ethylene-vinyl acetate copolymer and in which the film is apertured.

5. A film according to claim 4 which is in the form of a net and in which the area of apertures is 10% to 50% of the total area of the film.

6. A film according to claim 1 in which the polymer blend comprises 40% to 90% by weight of ethylene-vinyl acetate copolymer.

7. A film according to claim 1 in which the incompatible polymer comprises polystyrene.

8. A wound dressing or hygenic absorbent pad which comprises a moisture vapor transmitting elastomeric film which comprises a blend of incompatible polymers and contains voids within the film, said voids not providing a continuous pathway through the film, and wherein the blend comprises a continuous matrix of ethylene-vinly acetate copolymer within which the incompatible polymer forms a discrete particulate phase.

9. A wound dressing according to claim 8 which comprises a moisture vapor transmitting elastomeric film coated on one side with an adhesive layer.

10. A wound dressing according to claim 2 wherein one surface is coated with adhesive.

11. A wound dressing according to claim 10 in which the adhesive is moisture vapor transmitting and the dressing has a moisture vapor transmission rate of at least 500 g/m²/24 hours at 37° C. at 100% to 10% relative humidity difference.

12. A wound dressing according to claim 10 in which the adhesive is continuous and is 12.5 to 75 microns thick.

13. A wound dressing according to claim 12 in which the adhesive comprises an acrylate ester copolymer.

14. A process for producing a moisture vapor transmitting elastomeric film which comprises a blend of incompatible polymers and contains voids within the film, said voids not providing a continuous pathway through the film, and wherein the blend comprises a continuous matrix of ethylene-vinyl acetate copolymer within which the incompatible polymer forms a discrete particulate phase, which process comprises forming a film from the blend of ethylene-vinyl acetate and incompatible polymer, cold drawing the film until voiding occurs and allowing the drawn film to contract.

15. A process according to claim 14 which additionally comprises forming in the film of ethylene-vinyl acetate copolymer and incompatible polymer thicker and thinner areas and stretching the film until apertures form in the thinner areas.

* * * * *